(12) United States Patent
Boukhny et al.

(10) Patent No.: US 7,870,505 B2
(45) Date of Patent: *Jan. 11, 2011

(54) GRAPHICAL USER INTERFACE FOR PHACOEMULSIFICATION SURGICAL SYSTEM

(75) Inventors: Mikhail Boukhny, Laguna Niguel, CA (US); David A. Thoe, Laguna Hills, CA (US)

(73) Assignee: Alcon, Inc., Hunenberg (CH)

( * ) Notice: Subject to any disclaimer, the term of this patent is extended or adjusted under 35 U.S.C. 154(b) by 1310 days.

This patent is subject to a terminal disclaimer.

(21) Appl. No.: 11/401,659

(22) Filed: Apr. 11, 2006

(65) Prior Publication Data

US 2006/0236242 A1  Oct. 19, 2006

Related U.S. Application Data

(60) Provisional application No. 60/671,879, filed on Apr. 15, 2005.

(51) Int. Cl.
*G06F 3/048* (2006.01)

(52) U.S. Cl. .................... 715/810; 604/22; 600/471; 606/6

(58) Field of Classification Search ................ 715/761, 715/700, 810–847; 604/22; 600/471; 606/4–6
See application file for complete search history.

(56) References Cited

U.S. PATENT DOCUMENTS

| | | | | | |
|---|---|---|---|---|---|
| 4,812,996 A | * | 3/1989 | Stubbs | ................ | 702/123 |
| 4,933,843 A | * | 6/1990 | Scheller et al. | ................ | 604/22 |
| 5,249,121 A | * | 9/1993 | Baum et al. | ................ | 606/1 |
| 5,371,851 A | * | 12/1994 | Pieper et al. | ................ | 345/501 |
| 5,580,347 A | * | 12/1996 | Reimels | ................ | 604/30 |
| 5,853,367 A | * | 12/1998 | Chalek et al. | ................ | 600/437 |
| 5,898,434 A | * | 4/1999 | Small et al. | ................ | 715/810 |
| 5,910,139 A | * | 6/1999 | Cochran et al. | ................ | 606/1 |
| 6,066,129 A | * | 5/2000 | Larson | ................ | 606/10 |
| 6,179,829 B1 | * | 1/2001 | Bisch et al. | ................ | 606/1 |
| 6,251,113 B1 | | 6/2001 | Appelbaum | | |
| 6,319,220 B1 | * | 11/2001 | Bylsma | ................ | 604/22 |
| 6,428,508 B1 | * | 8/2002 | Ross | ................ | 604/118 |

(Continued)

OTHER PUBLICATIONS

European Search Report for Application No. 06112595.1, filed Apr. 13, 2006, Published Oct. 18, 2006, Patent No. 1712209, Granted Apr. 1, 2009, 2 pages.

(Continued)

*Primary Examiner*—Boris Pesin
*Assistant Examiner*—William Wong
(74) *Attorney, Agent, or Firm*—Darien Reddick

(57) ABSTRACT

A graphical user interface for use in phacoemulsification surgical systems that allows a user to select different pulse modes by touching portions of the display screen. The user interface includes first and second display elements. One display element includes a representation of the on-time of the pulses, and the other display element includes a representation of the off-time. The representations show how the on-time and off-time change relative to a position of a controller, such as a foot pedal. The representation show a constant time, or that a time increases or decreases as the foot pedal is pressed. To select a pulse mode, a user can scroll through different pulse representations by touching the screen at the display elements. The selected pulse mode can be continuous, pulse, burst, or a combination or derivation thereof.

1 Claim, 12 Drawing Sheets

U.S. PATENT DOCUMENTS

| | | | |
|---|---|---|---|
| 6,507,796 B2 * | 1/2003 | Alexander | 702/70 |
| 6,659,998 B2 * | 12/2003 | DeHoogh et al. | 606/1 |
| 6,707,474 B1 * | 3/2004 | Beck et al. | 715/771 |
| 6,783,523 B2 * | 8/2004 | Qin et al. | 606/1 |
| 7,077,820 B1 * | 7/2006 | Kadziauskas et al. | 604/22 |
| 7,225,405 B1 * | 5/2007 | Barrus et al. | 715/716 |
| 2002/0045887 A1 | 4/2002 | DeHoogh | |
| 2002/0054144 A1 * | 5/2002 | Morris-Yates | 345/809 |
| 2004/0024384 A1 * | 2/2004 | Novak | 606/1 |
| 2004/0092922 A1 * | 5/2004 | Kadziauskas et al. | 606/27 |
| 2005/0080348 A1 * | 4/2005 | Stahmann et al. | 600/529 |
| 2006/0074405 A1 * | 4/2006 | Malackowski et al. | 606/1 |
| 2006/0235307 A1 * | 10/2006 | Boukhny et al. | 600/471 |
| 2006/0248477 A1 * | 11/2006 | Boukhny et al. | 715/840 |

OTHER PUBLICATIONS

European Search Report for Application No. 07111481.3, filed Apr. 13, 2006, Published Sep. 26, 2007, Publication No. 1837002, 2 pages.

* cited by examiner

"PRIOR ART"

"PRIOR ART"

"PRIOR ART"

"PRIOR ART"

620

640

610

610

600

630

GRAPHICAL USER INTERFACE FOR PHACOEMULSIFICATION SURGICAL SYSTEM

CROSS-REFERENCE TO RELATED APPLICATIONS

This application claims priority under 35 U.S.C. §119 to U.S. Provisional Patent Application No. 60/671,879, filed Apr. 15, 2005, the entire contents of which are incorporated herein by reference.

FIELD OF THE INVENTION

The invention relates generally to graphical user interfaces for surgical systems, and, more particularly, to graphical user interfaces for phacoemulsification surgical systems that include representations of the functions or behavior of the on-time and the off-time of pulses. The on-time and off-time functions can be changed by touching the screen.

BACKGROUND

Modern surgical systems, and in particular, modem ophthalmic surgical systems, are designed to monitor and display multiple parameters of a surgical device or instrument that is connected to the surgical system and controlled by the surgeon through the use of a foot pedal. Such systems can be complex given the multiple parameters that must be displayed and controlled by a surgeon, particularly during a surgical procedure.

Certain known phacoemulsification systems allow for application of ultrasound energy at a fixed level. For example, the foot pedal acts as an on/off switch to activate and deactivate ultrasound energy that is at a particular power level. When the foot pedal is pressed, the device is activated and the power level is constant or "continuous."

"Continuous" power systems were improved by the introduction of "linear" mode, which allows a surgeon to control power in a variable manner. A surgeon controls power based on the foot pedal position so that the power is proportional to or linear with respect to the displacement of the foot pedal. Thus, more power is provided as the surgeon presses the foot pedal, and less power is provided as the foot pedal is released.

Further improvements involved the introduction of "pulse" mode. In "pulse" mode, phacoemulsification energy is provided in periodic pulses at a constant duty cycle. The surgeon increases or decreases the amount of power by pressing or releasing the foot pedal, which increases or decreases the amplitude of the fixed-width pulses.

Further enhancements involved the introduction of "burst" mode. In "burst" mode, power is provided through a series of periodic, fixed width, constant amplitude pulses. Each pulse is followed by an "off" time. The off-time is varied by the surgeon by pressing and releasing the foot pedal to adjust power.

In order to accommodate continuous, "linear," "pulse" and "burst" mode and their operating parameters, known user interfaces of phacoemulsification systems typically include several human actionable controllers and fields or elements that occupy particular positions on a display screen. Some known user interfaces include buttons, arrows, switches, bars and/or knobs for setting desired numeric values of operating characteristics of the surgical system. Certain parameters are fixed or have a constant value regardless of the foot pedal position, whereas other parameters vary, e.g., vary linearly, with the foot pedal. The interface is manipulated by a surgeon to provide control signals to the surgical instruments which, in turn, control the modes or types of pulses that are generated.

FIGS. 1 and 2 illustrate one known interface for a phacoemulsification system. A surgeon manually selects the power mode from a selection bar or menu 10. In this interface, the menu 10 includes "Ultrasound Continuous," "Ultrasound Pulse," and "Ultrasound Burst" menu bars 12, 14 and 16, respectively. In the example illustrated in FIGS. 1 and 2, the continuous power menu bar 12 is selected from the menu 10. The power limit is represented in a window or field 20. The maximum amount of continuous power or the power limit is adjusted using up/down arrows 24. In this example, the continuous power limit is selected to be "35" or 35% of the maximum allowed power. The continuous power varies linearly, as shown by the line 26 in the background of the power limit window 20. The current power level is also provided in a window 28. In the illustrated example, the current power is "0" or 0% since the screen represents current power when the foot pedal is released. Pressing the foot pedal results in power increasing linearly from 0% to 35%. When the surgeon wants to change from "continuous" mode to another mode, the surgeon selects the "ultrasound continuous" bar 12 so that the menu 10 of available pulse modes is displayed. The surgeon can then select another mode from the menu 10.

For example, FIG. 3 illustrates that "Ultrasound Pulse" menu bar 14 is selected from the menu 10. A surgeon manually selects a maximum power level of 35%, which varies linearly as the foot pedal is pressed and released. In addition, the interface includes a window 30 for the pulse rate or pulses per second (pps) and a window 40 for the "on-time" (% Time on). The number of pulses per second (pps) and the on-time, however, do not vary with movement of the foot pedal. Rather, the pps is fixed at 14 pps using arrows 34, and the on-time is fixed at 45% using arrows 44. Thus, the pps and on-time values do not change when the foot pedal is displaced and must be manually adjusted by the surgeon using arrows 34 and 44. Power increases linearly from 0-35% as the foot pedal is pressed, and is delivered at a fixed rate of 14 pulses per second at a fixed 45% duty cycle.

Referring to FIGS. 2 and 4, when "Ultrasound Burst" mode is selected from the menu 10, the same limit and power window 28 and limit window 20 are provided. The power varies linearly with the foot pedal, as discussed above. Rather than pps and on time windows 30 and 40 (as shown in FIG. 3), the interface displays a window 50 for on-time or On (ms) and a window 60 for off time or Off (ms) when in "burst" mode. The On (ms) and Off (ms) values are fixed and do not change when the foot pedal is moved. The on-time (ms) is fixed at 70 ms using arrows 54. In this "burst" mode, the power increases from 0-40% as the foot pedal is depressed by changing the "off-time", and the duration of each pulse remains a constant 70 ms throughout displacement of the foot pedal. Thus, when changing from "pulse" mode to "burst" mode, different parameters are adjusted. In "pulse" mode, the parameters are pps and % on-time, and in "burst" mode, the parameters are on-time and off-time (ms).

While known interfaces have been successfully used to perform phacoemulsification procedures in the past, they can be improved. Particularly, the visual and functional aspects of interfaces can be enhanced so that surgeons can control different pulse modes and can easily switch between different modes. User interfaces should include additional controllable display elements that allow different modes and their parameters to be quickly and easily adjusted. These improvements should be made without unduly complicating the user interface and how it functions. Further, interfaces should be capable of effectively representing various operating parameters of various ultrasound driving modes, including continuous, linear, pulse, burst, and new modes, which can be combinations and modifications of known modes.

BRIEF DESCRIPTION OF THE DRAWINGS

A more complete understanding of embodiments and the advantages thereof may be acquired by referring to the following description, taken in conjunction with the accompanying drawings, in which like reference numbers indicate like features and wherein.

DETAILED DESCRIPTION OF ILLUSTRATED EMBODIMENTS

Figure 1:
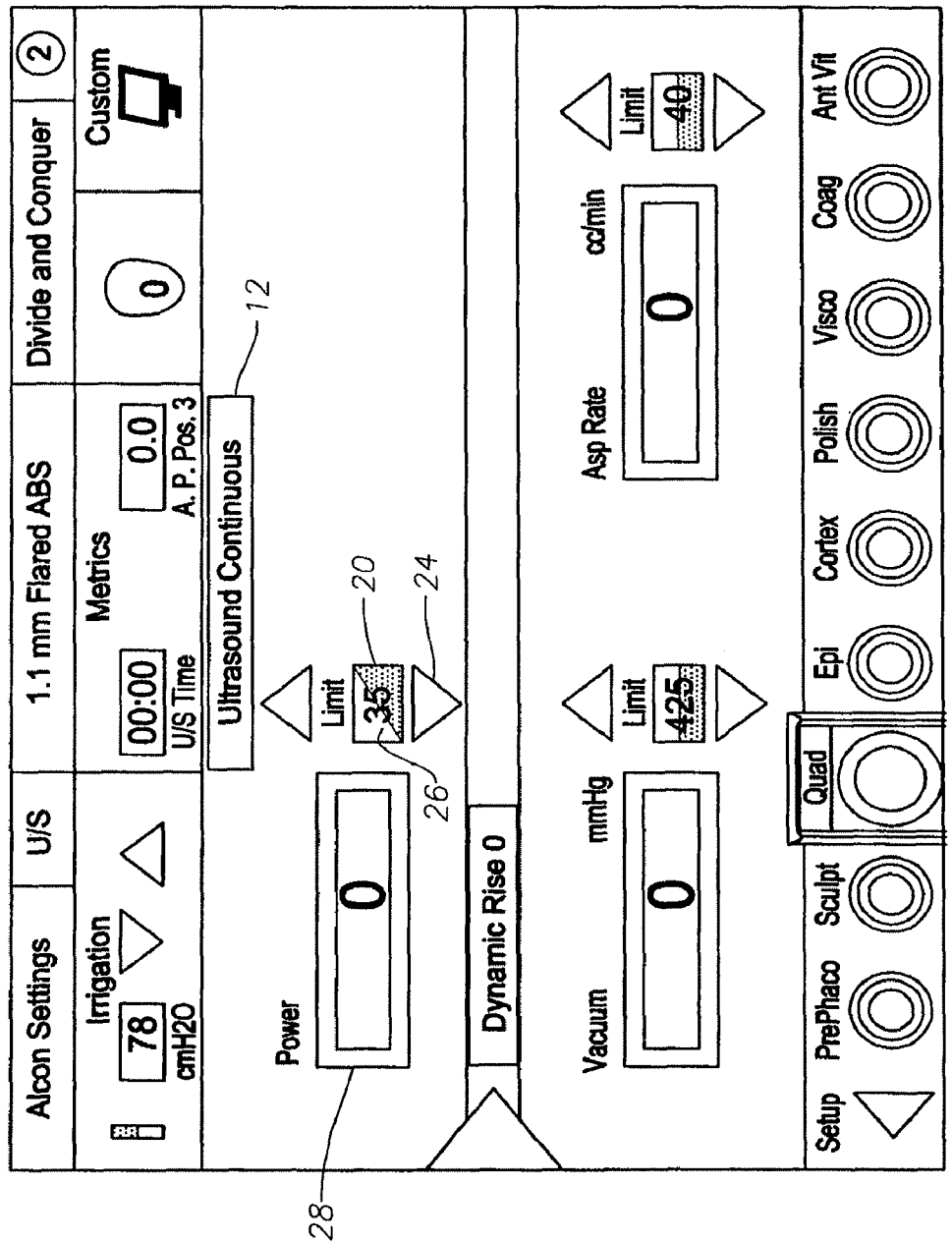
FIG. 1 illustrates a known graphical user interface for use with a phacoemulsification surgical system in "continuous" mode.
Figure 2:
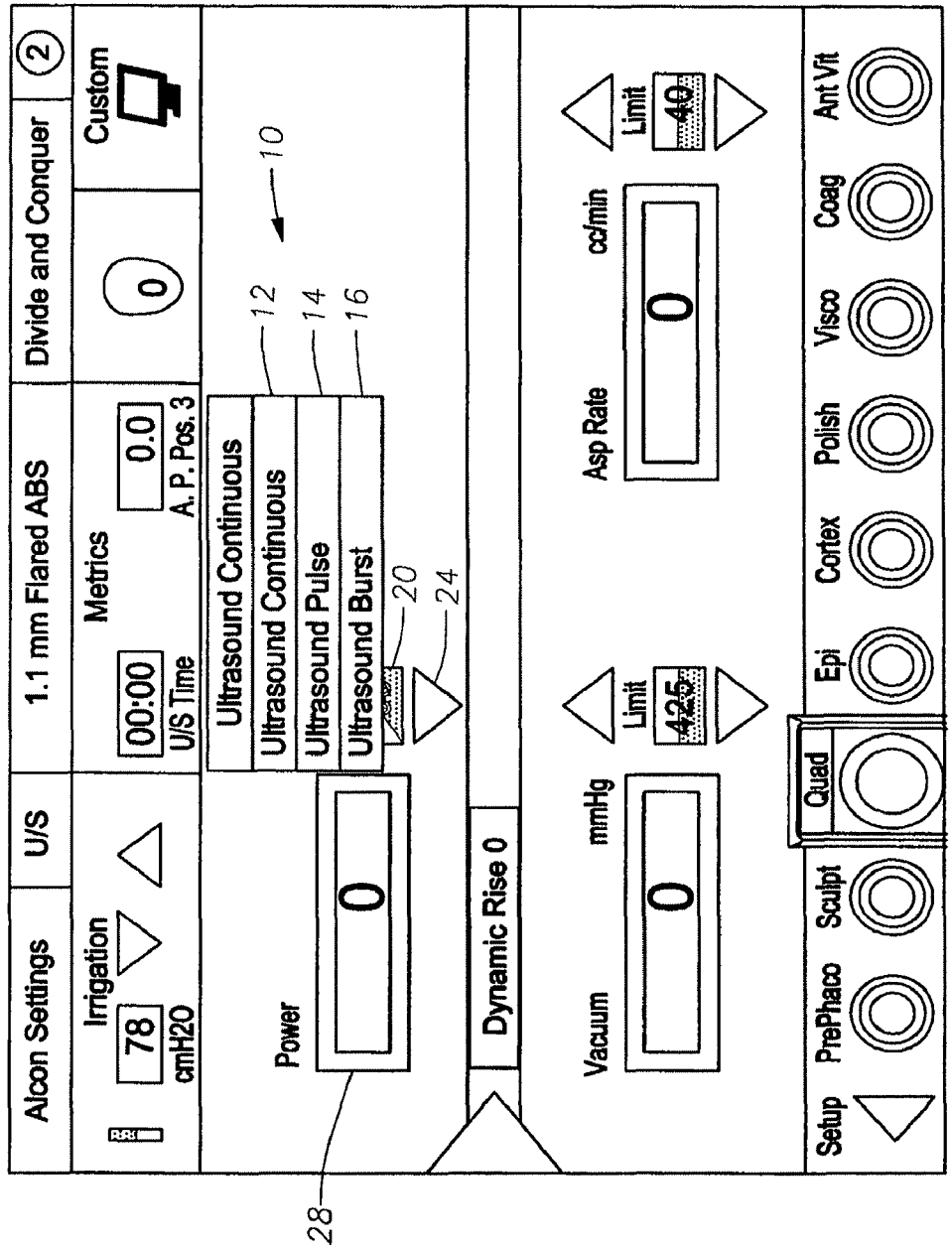
FIG. 2 illustrates the interface shown in FIG. 1 after the "continuous" mode menu bar is selected to generate a drop down menu of available pulse modes.

In the following description, reference is made to the accompanying drawings which form a part hereof, and which show by way of illustration specific embodiments in which the invention may be practiced. It is to be understood that changes may be made without departing from the scope of invention.

Embodiments of the invention are directed to a graphical user interface that provides improved control over the ultrasound driving or pulse modes that are generated by a phacoemulsification surgical system and improved control over the parameters of the different pulse modes. Embodiments provide display elements that can be quickly and easily selected and adjusted by a surgeon to select different modes, while allowing various pulse parameters to be adjusted to customize the various modes. The pulse modes that can be selected include "Continuous," "Pulse" and "Burst" modes and, in addition, hybrid or combination modes that were not previously readily available for use in phacoemulsification systems. Representations of characteristics or the functions of pulses are displayed in display elements. The representations can be changed by touching a display screen at a particular display element to generate a menu from which a representation of a pulse characteristic, such as the on-time and the off-time, can be selected by the user. Alternatively, a user can scroll through different representations of the characteristics or function of the on-time and the off-time of the pulses. The representation that is selected represents the function or behavior of the pulse characteristic, e.g., whether and how the on-time and the off-time vary in response to displacement of a controller, such as a foot pedal, and the types and characteristics of pulses that are generated by the phacoemulsification system.

Embodiments of the invention provide improvements over known interfaces by allowing on-time and the off-time representations to be adjusted so that they increase linearly, increase non-linearly, decrease linearly, decrease non-linearly, and remain substantially constant relative to displacement of a foot pedal, which, in turn, determine whether the on-time and/or off-time decrease or increases linearly or non-linearly or remain constant. Different pulse modes can be generated by selecting the manner in which the on-time and the off-time vary (or do not vary). For example, nine different pulse modes can be selected when the on-time and the off-time each can increase, decrease or remain constant in response to movement of the foot pedal. The power limit, the on-time and the off-time, can be adjusted using up/down arrows and other suitable adjustment mechanisms.

Persons skilled in the art will appreciate that embodiments of the invention can be utilized with other surgical equipment including, but not limited to, neurosurgery equipment, where control of various instruments is also performed with a remote foot pedal. For purposes of explanation, not limitation, this specification describes embodiments related to phacoemulsification procedures and their associated operating parameters.

Figure 5:
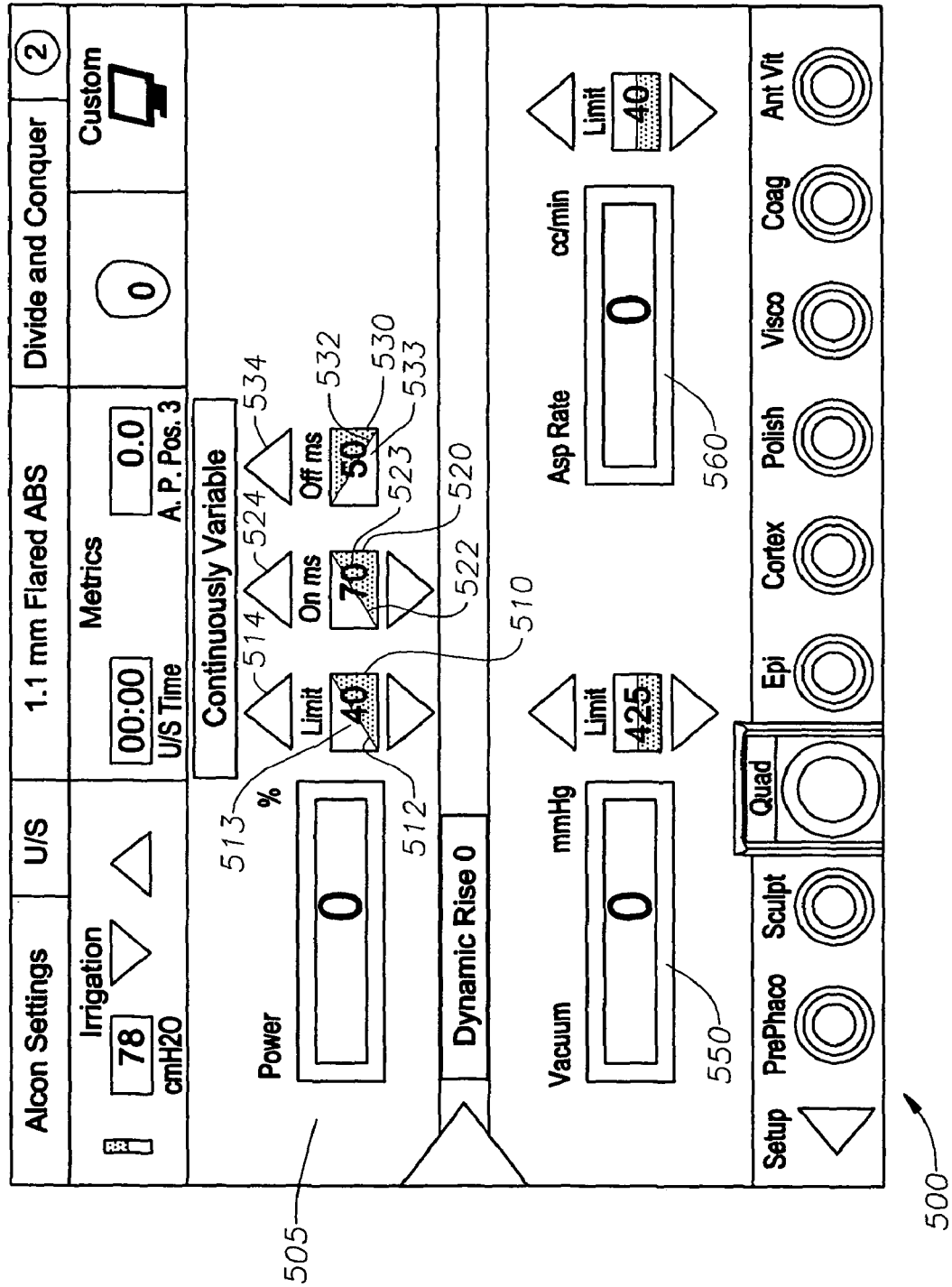
FIG. 5 illustrates a graphical user interface according to one embodiment of the invention that includes representations of the functions of pulse on-time and off-time.

Referring to FIG. 5, a user interface 500 for a phacoemulsification surgical system according to one embodiment is displayed on a display screen 505 of the system. The interface 500 includes a maximum power or power limit display element 510, an on-time display element 520, and an off-time display element 530. The current power level, as controlled by the foot pedal, is shown in a current power display element 540. The interface 500 also includes other display elements and adjustments for other phacoemulsification surgical parameters, such as aspiration flow rate (Asp Rate) 560 and vacuum limit pressure (Vacuum) 550, as are known in the art. Operation of these other display elements 550 and 560 is not discussed further in this specification. Pressing and releasing the foot pedal controls the operation of the surgical devices according to the corresponding operating parameters and parameter values that are represented in the interface 500 and programmed in the system.

In the illustrated embodiment, the display elements 510, 520 and 530 are rectangle-shaped display elements. Indeed, other shapes besides rectangular shapes can be utilized, and rectangle-shaped display elements are provided for purposes of illustration, not limitation. The power display element 510 includes a representation 512 of the behavior or function of the power relative to a position of the foot pedal. The on-time display element 520 includes a representation 522 of the behavior or function of the on-time of the pulses relative to a position of the foot pedal. The off-time display element 530 includes a representation 532 of the behavior or function of the off-time of the pulses relative to a position of the foot pedal. The graphic representations can be easily and quickly selected and adjusted by a surgeon before and during surgery.

Figure 6:
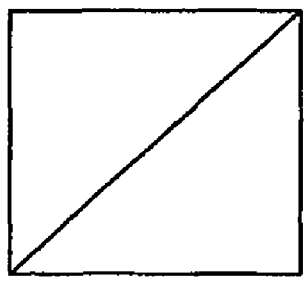
FIG. 6 illustrates exemplary linear and non-linear representations of pulse characteristics relative to a position of a foot pedal according to one embodiment.
Figure 6:
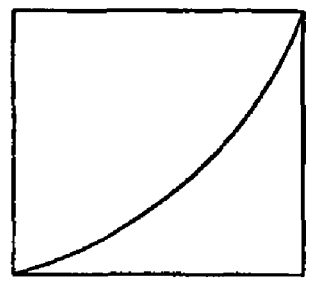
Figure 6:
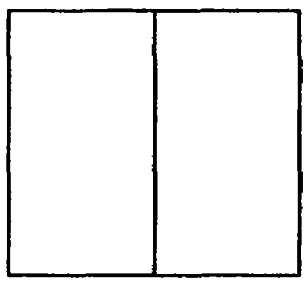
Figure 6:
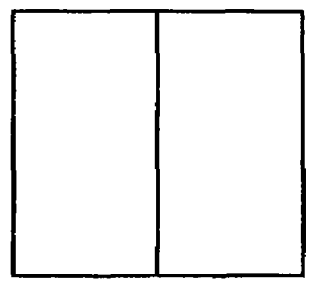
Figure 6:
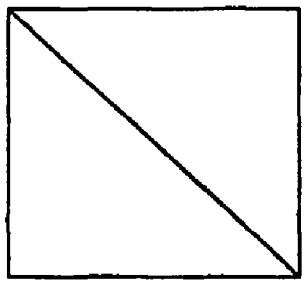
Figure 6:
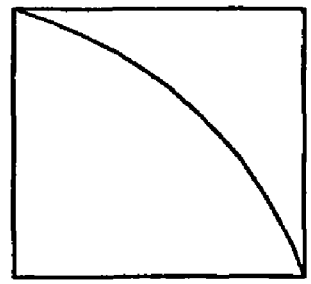

Referring to FIG. 6, a representation of a pulse characteristic can have various shapes depending on the desired relationship or function between the pulse parameter and the position of the foot pedal. As shown in FIG. 6, a representation of a characteristic of a pulse can be linear or non-linear representation, to represent a linear or non-linear function of the power, on-time and/or off-time. A linear representation can be an increasing linear representation 600, a horizontal or constant linear representation 610, and a decreasing linear representation 620. A non-linear representation can be an increasing non-liner representation 630 and a decreasing non-linear representation 640.

Exemplary non-linear representations include exponential and polynomial representations so that the power, on-time and/or off-time varies exponentially or in accordance with a polynomial with movement of the foot pedal.

Figure 8:
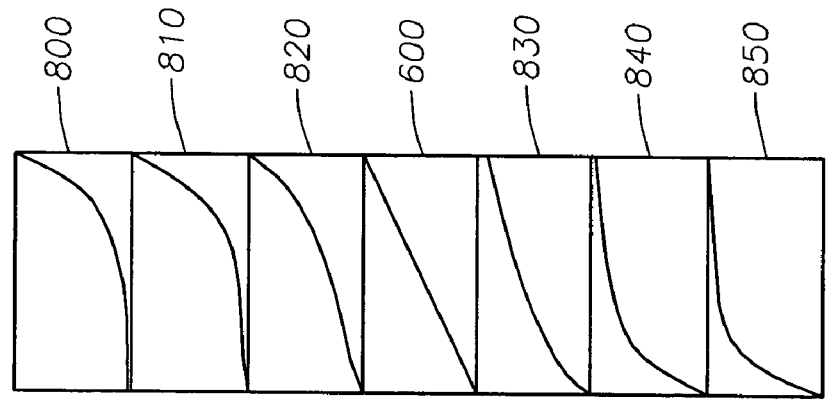
FIG. 8 illustrates exemplary non-linear representations of on-time and off-time that increase relative to a position of a foot pedal.
Figure 7:
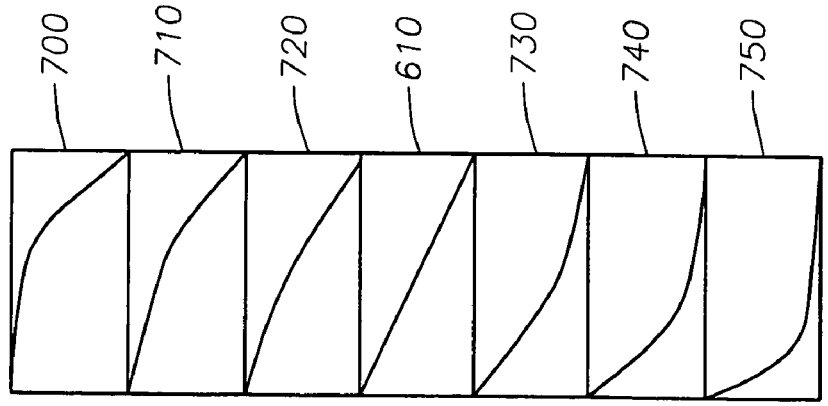
FIG. 7 illustrates exemplary non-linear representations of on-time and off-time that decrease relative to a position of a foot pedal.

FIG. 7 illustrates exemplary non-linear representations. Non-linear representations 700-750 decrease non-linearly in different manners. Representations 700-720 and corresponding functions of the power, on-time and/or off-time decrease less rapidly when the foot pedal is initially depressed, and decrease more rapidly as the foot pedal is depressed further. Representations 730-750 and corresponding functions of the power, on-time and/or off-time decrease more rapidly when the foot pedal is initially depressed, and decrease more slowly as the foot pedal is depressed further. FIG. 8 illustrates similar relationships with increasing representations of the behavior or functions of a power, on-time and/or off-time.

For purposes of explanation and illustration, not limitation, this specification refers to linear representations, e.g., increasing linear, constant, and decreasing linear representations and related linear functions of power, on-time and/or off-time. Persons skilled in the art will appreciate that the power, on-time and off-time can be controlled with linear representations, non-linear representations and combinations thereof. Persons skilled in the art will also appreciate that a linear representation may represent a characteristic of a pulse that is substantially linear and that includes some non-linear components in actual practice. For example, the relationship between the actual power and the position of the foot pedal may not be exactly linear due to mapping the foot pedal position to the amount of power that is generated. Thus, there may be some deviations from a truly "linear" representation in practice due to mapping and other factors.

In the embodiments shown in FIG. 6, an increasing linear representation 600 extends from a bottom left corner to a top right corner of a display element to illustrate that the parameter being represented increases linearly as the foot pedal is pressed and decreases linearly as the foot pedal is released. A horizontal or constant linear representation 620 extends between opposite sides of a display element and illustrates that the parameter being represented remains substantially constant at various foot pedal positions. A decreasing linear representation 610 extends from a bottom left corner to a top right corner of a display element and illustrates that the parameter being represented decreases linearly as the foot pedal is pressed and increases linearly as the foot pedal is released. In alternative embodiments, increasing and decreasing linear representations 600 and 610 and corresponding functions of the pulse parameter may extend between a side and a corner of a display element or two sides of a display element, while still showing an increasing or decreasing relationship. This may represent, for example, that the starting value of the pulse parameter, such as the on-time and the off-time, is a non-zero value.

Initial and minimum values of the power, on-time and off-time can be set or programmed as necessary. The system can be configured so that the minimum power value is 0% or another desired value when the foot pedal is in its home position, e.g., when the foot pedal is released. For example, the initial on-time or, alternatively, the minimum on-time, can be 0 ms or another desired value. Similarly, the initial off-time or, alternatively, the minimum off-time, can be 0 ms or another desired value. Initial values or, alternatively, minimum values, can set using another interface screen or programming the values into the system.

Referring again to FIG. 5, a display element includes a value for a pulse parameter. For example, the power limit display element 510 includes a power value 513, the on-time display element 520 includes an on-time value 523 and the off-time display element includes an off-time value 533. The values are adjusted using respective up/down arrows 514, 524 and 534 or other suitable adjustment mechanisms, such as slide bars. This specification refers to up/down arrows for purposes of illustration, not limitation. For example, if the function of on-time is an increasing function, then the on-time value represents the maximum on-time. The minimum on-time can be zero or another selected value. For example, the minimum value can be 20% of the maximum value. The starting value can be determined using a formula function or other techniques. As a further example, if the function of on-time is a decreasing function, then the on-time value represents the minimum on-time value when the foot pedal is fully depressed. The maximum on-time can be selected as appropriate. Similar controls apply to the off-time. The values represent the minimum or maximum values of each parameter when the foot pedal is fully depressed.

Thus, if the maximum value of the on-time is 70 ms and the on-time representation increases linearly, then the on-time increases linearly, from zero or a minimum value (e.g., 20% of 70 ms) to 70 ms as the foot pedal is pressed. If the on-time representation decreases linearly, then the on-time decreases from a maximum value to 70 ms in a linear manner as the foot pedal is pressed. Similarly, if the maximum value of the off-time is 70 ms and the off-time representation decreases linearly, then the off-time decreases from a maximum value of 70 ms in a linear manner as the foot pedal is pressed. If the off-time representation increases linearly, then the off-time increases from 0 ms or a minimum value to 70 ms in a linear manner as the foot pedal is pressed. As a further example, if the maximum value of the off-time is 50 ms, and the off-time representation is horizontal, then the off-time remains substantially constant at 50 ms at different foot level positions. If the maximum value of the on-time is 50 ms, and the on-time representation is horizontal, then the on-time remains substantially constant at 50 ms at different foot level positions.

In the illustrated embodiment, the values are superimposed over their respective representations. In other words, the representation appears in the background of a display element. For example, the value 513 is superimposed over the power representation 512, the value 523 is superimposed over the on-time representation 522 and the value 533 is superimposed over the off-time representation 532. In alternative embodiments, the representations can also be superimposed over the values depending on display preferences.

Figure 9:
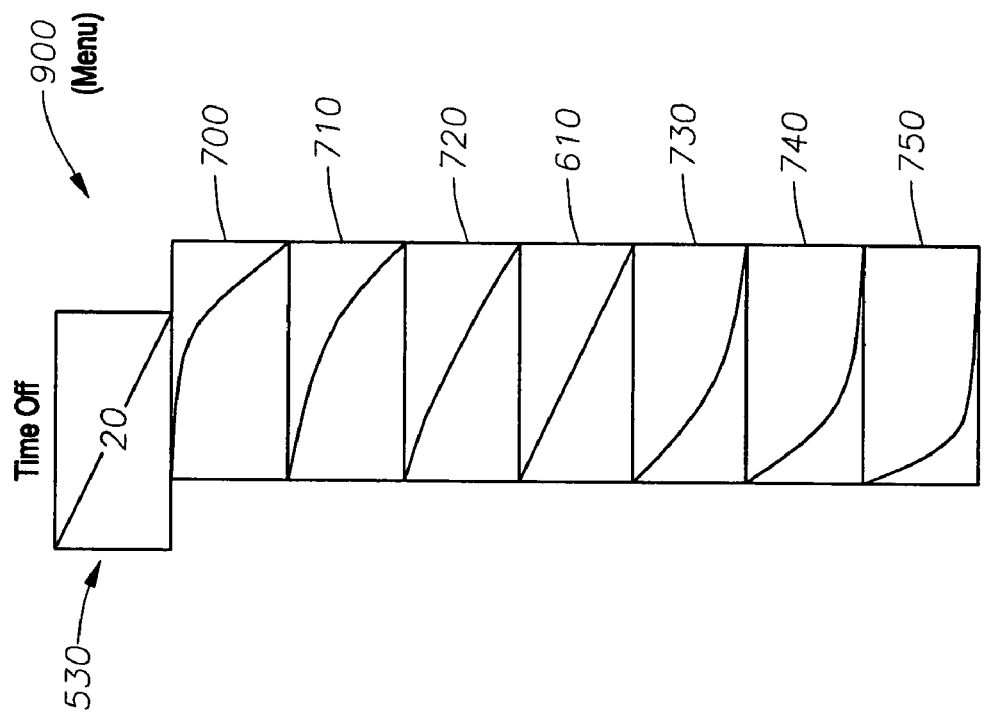
FIG. 9 illustrates a menu that includes representations of on-time and off-time according to one embodiment.

A surgeon can select and switch representations and the manner in which the power, on-time and off-time function in different manners. Referring to FIG. 9, according to one embodiment, the surgeon can touch the display screen at a display element so that a menu 900 of different representations is displayed. The surgeon can then select a new representation or function of the power, on-time and/or off-time from the menu 900. For example, referring to FIGS. 5 and 9, a surgeon can touch the display screen 505 at the off-time display element 530. As a result, a menu 900 of decreasing representations is displayed, and the surgeon can then select one of the representations from the menu 900. The selected representation represents how the pulse characteristic functions. Of course, the menu 900 can include different numbers of decreasing, increasing and constant or horizontal representations. FIG. 9 illustrates a menu 900 having decreasing representations for purposes of illustration, not limitation. Each of the power limit, on-time and off-time representations can be adjusted using a menu 900.

Figure 10:
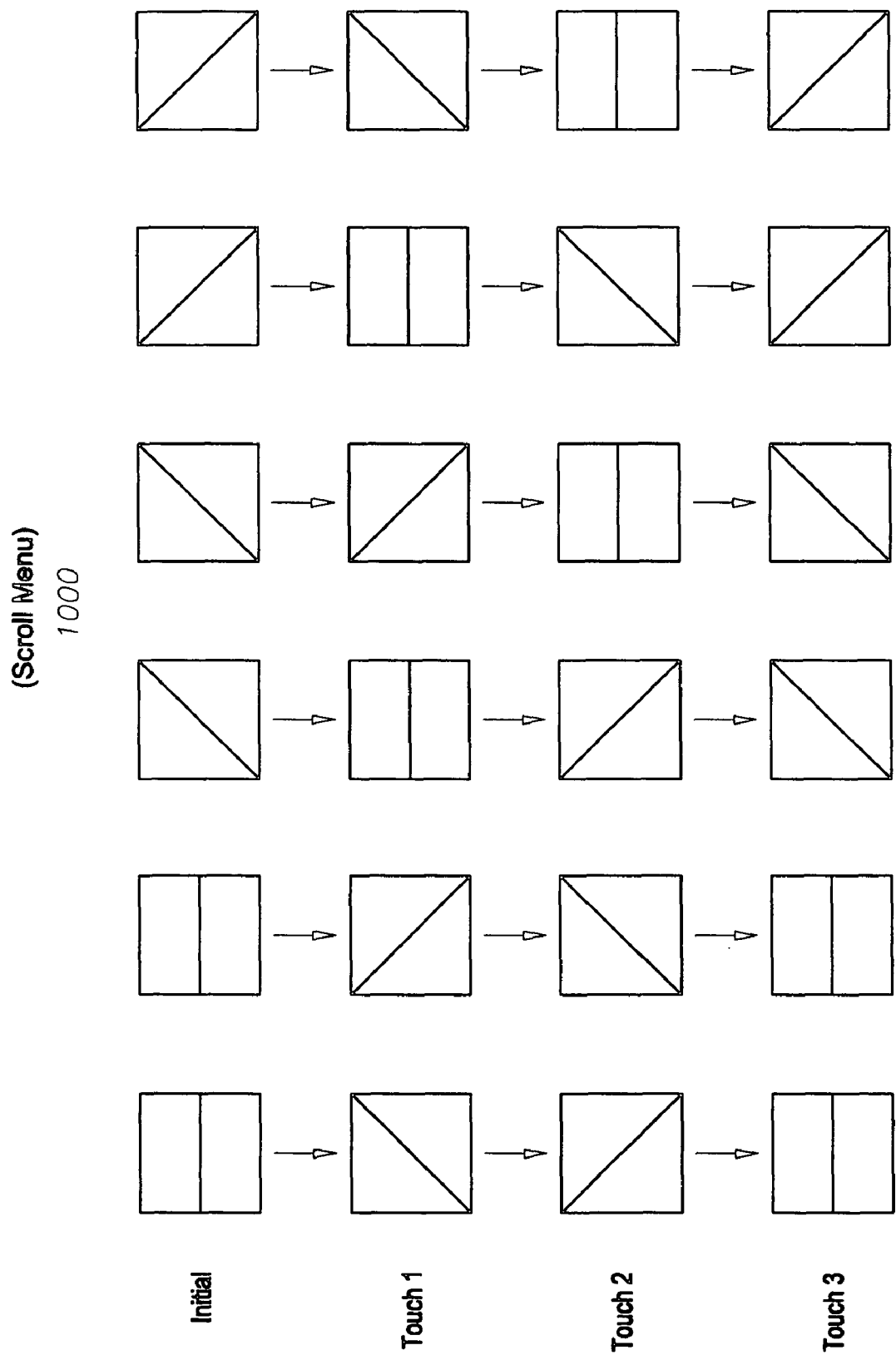
FIG. 10 illustrates exemplary sequences of displaying horizontal, increasing and decreasing on-time and off-time representations according to one embodiment in which a user can scroll through different representations.

Referring to FIG. 10, according to another embodiment, a surgeon can touch the display screen 500 at a display element to change the representation of the pulse characteristic to the desired representation using a scroll menu 1000. In this embodiment, each time the surgeon touches the display screen 505 at a particular display element, the representation of that pulse parameter changes to a new representation. In other words, the surgeon can scroll through different representations of pulse characteristics by touching the display screen 505 at the corresponding display element. Thus, in the embodiment shown in FIG. 10, different representations are shown to the surgeon individually rather than shown as a group or menu 900, as shown in FIG. 9.

The representations in a scroll menu can appear to the surgeon in different orders. For example, if the initial representation is a horizontal representation, a first touch (Touch 1) of a display element can change the horizontal representation to a linear increasing representation. The next touch (Touch 2) can change the linear increasing representation to a linear decreasing representation. The next touch (Touch 3) can change the linear increasing representation to the horizontal representation. Each of the power limit, on-time and off-time representations can be adjusted in this manner. FIG. 10 illustrates other sequences in which representations may be displayed to a surgeon in response to the surgeon touching the display screen at a display element. Further, alternative embodiments can include other numbers of representations and thus, other sequences of representations that are displayed.

Different ultrasound driving or pulse modes can be generated by the phacoemulsification system by selecting representations of the function or behavior of the power, on-time and off-time, using a menu shown in FIG. 9 or a scrolling menu shown in FIG. 10.

According to one embodiment, the on-time and the off-time can each be assigned three different representations: linear increasing, linear horizontal or constant, and linear decreasing.

Figure 11:
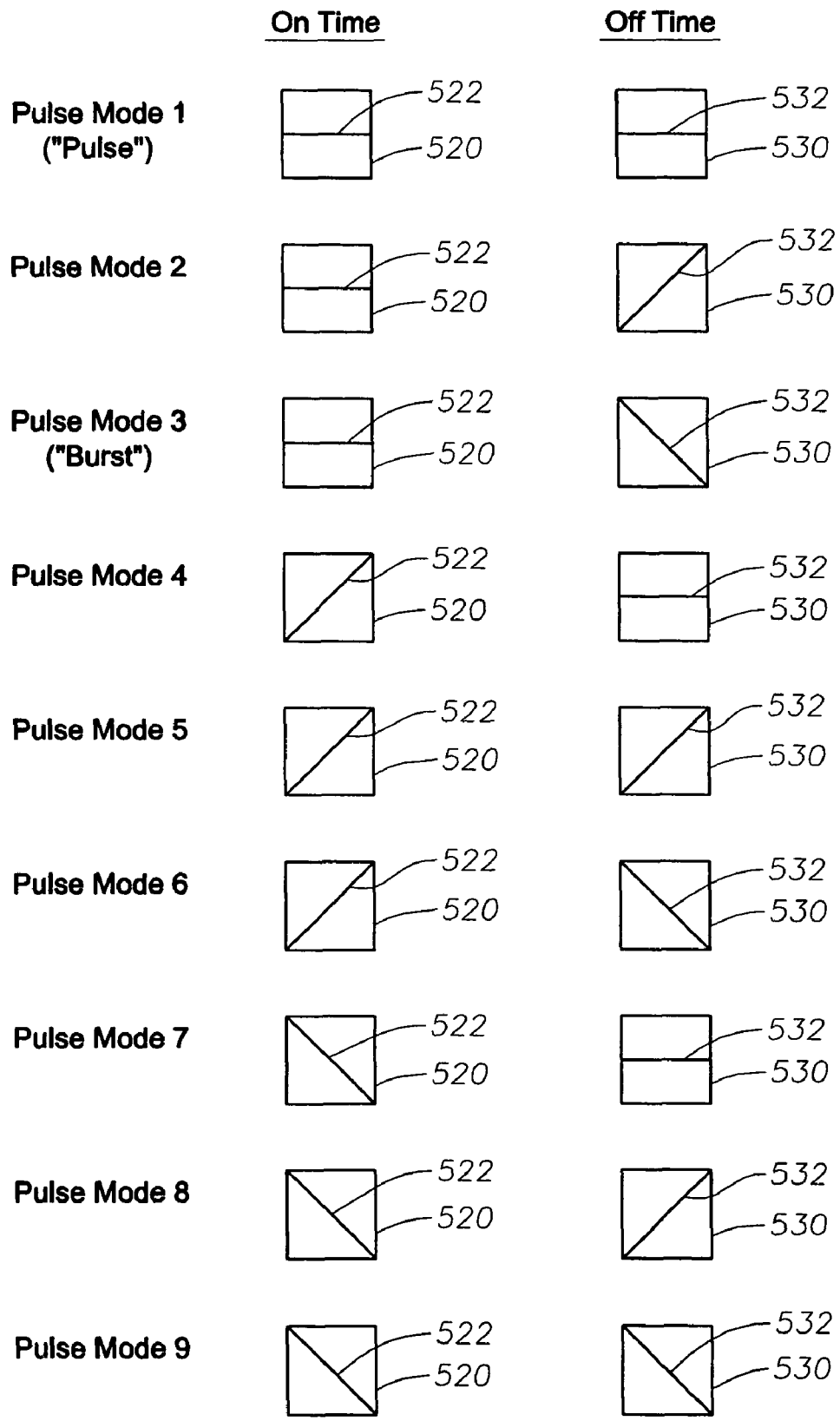
FIG. 11 illustrates nine different pulse modes that can be implemented by selecting one of three on-time representations and one of three off-time representations according to one embodiment.

Referring to FIG. 11, the total number of possible modes can be determined by multiplying the number of on-time representations and the number of off-time representations. In this embodiment, a surgeon can program nine different pulse modes. Indeed, the number of modes can change when using different numbers of representations.

In Mode 1, both the on-time and the off-time remain substantially constant when the foot pedal is pressed due to the horizontal representations. In Mode 2, the on-time remains substantially constant and the off-time increases linearly in response to the foot pedal being pressed. In Mode 3, the off-time remains substantially constant and the off-time decreases linearly in response to pressing the foot pedal. In Mode 4, the on-time increases linearly and the off-time remains substantially constant in response to pressing the foot pedal. In Mode 5, both the on-time and the off-time increase linearly as the foot pedal is pressed. In Mode 6, the on-time increases linearly and the off-time decreases linearly in response to the foot pedal being pressed. In Mode 7, the on-time decreases linearly and the off-time remains substantially constant in response to pressing the foot pedal. In Mode 8, the on-time decreases linearly and the off-time increases linearly in response to the foot pedal being pressed. In Mode 9, both the on-time an the off-time decrease linearly as the foot pedal is pressed. A surgeon can select one of the nine modes depending on the particular application according to one embodiment. FIGS. 12-19 illustrate exemplary implementations of selected modes. For purposes of explanation, FIGS. 12-19 illustrate only the power, on-time and off-time representations and related values.

Figure 3:
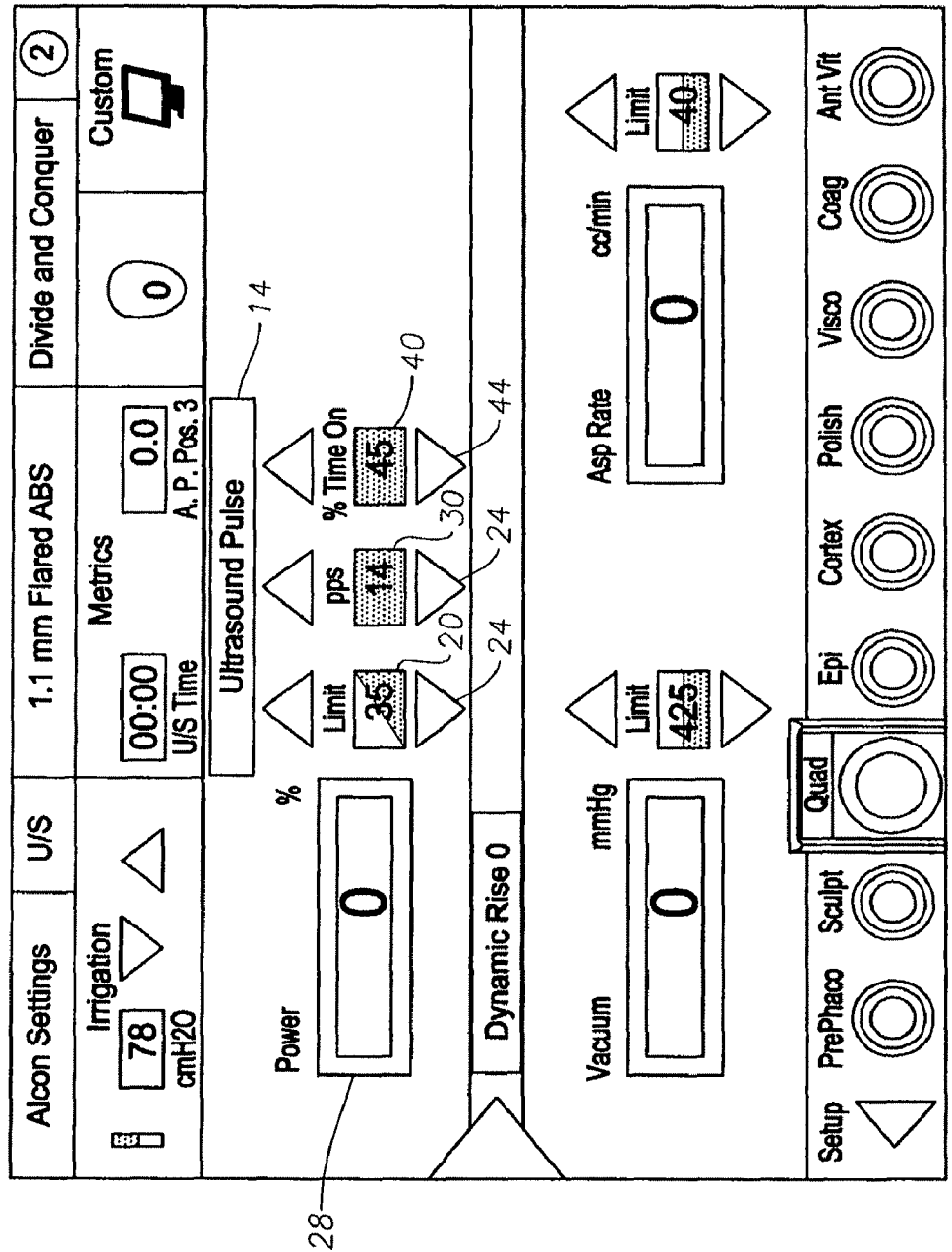
FIG. 3 illustrates the interface shown in FIG. 2 after the "Ultrasound Pulse" menu bar is selected from the menu.
Figure 4:
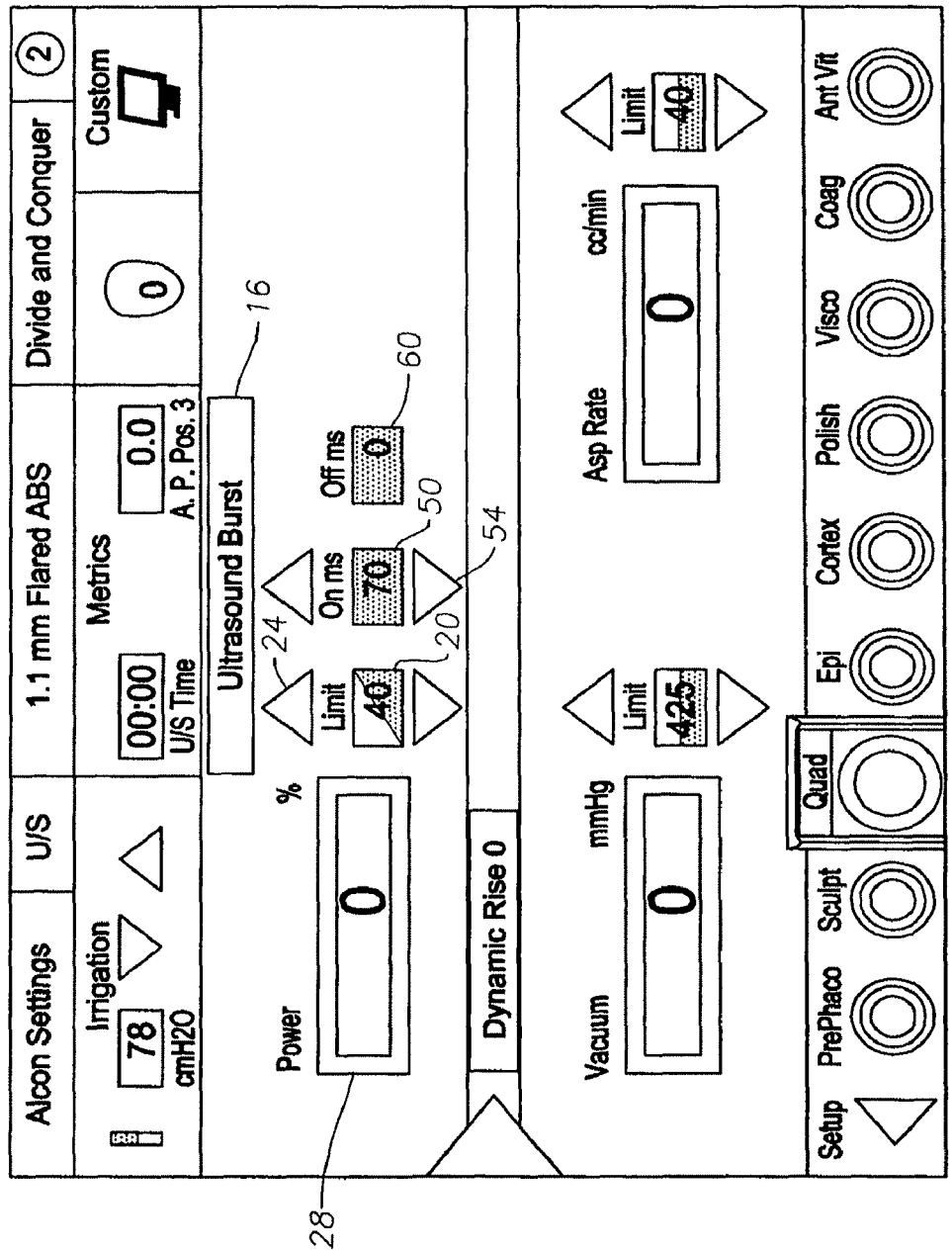
FIG. 4 illustrates the interface shown in FIG. 2 after the "Ultrasound Burst" menu bar is selected from the menu.
Figure 12:
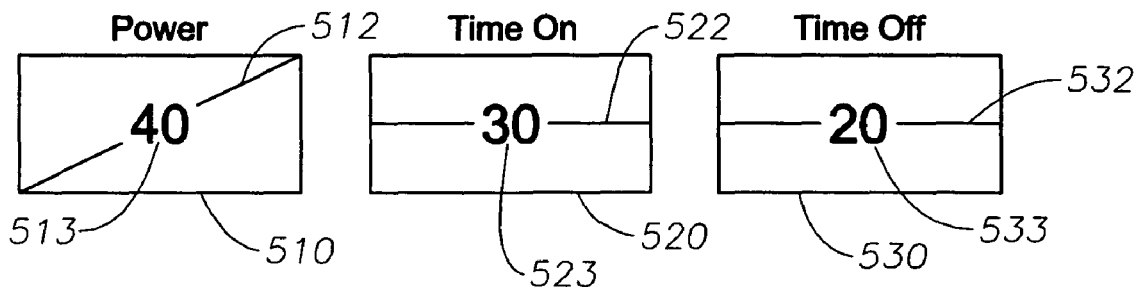
FIG. 12 illustrates an interface according to one embodiment that is set for "pulse" mode by selecting a constant on-time and a constant off-time.

FIG. 12 illustrates an exemplary implementation of Mode 1, which is commonly referred to as "Pulse" mode. In "Pulse" mode, phacoemulsification power is provided in periodic pulses at a constant duty cycle. The surgeon can increase or decrease the amount of power by pressing or releasing the foot pedal, which increases or decreases the amplitude of the fixed-width pulses. In known interfaces, such as the interface shown in FIG. 3, "Pulse" mode is typically set using the pulse rate expressed in pulses per second (pps) and the duty cycle or on-time, which is expressed in % time on. Embodiments of the invention use on-time and off-time to represent pulses in "Pulse" mode. Power increases to a maximum value of 40% as the foot pedal is depressed, whereas the on-time remains fixed at 30 ms and the off-time remains fixed at 20 ms.

Figure 13:
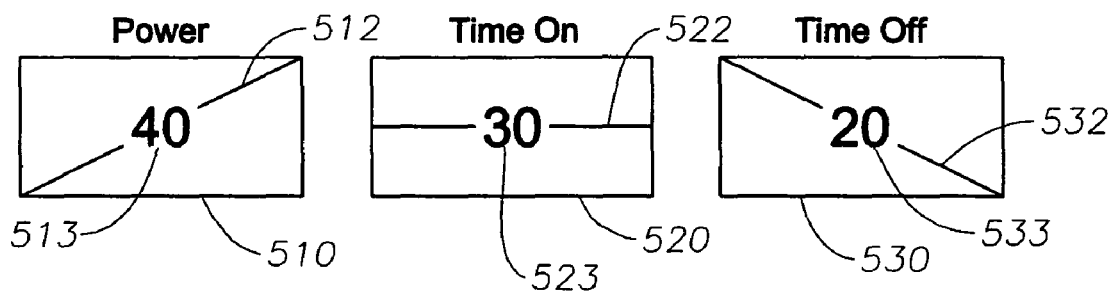
FIG. 13 illustrates an interface according to one embodiment that is set for a "burst" mode by selecting a constant on-time and a decreasing off-time relative to foot pedal displacement.

FIG. 13 illustrates an exemplary implementation of Mode 3, which is commonly referred to as "Burst" mode. In "Burst" mode, power is provided through a series of periodic, fixed width, constant amplitude pulses. Each pulse is followed by an "off" time. The off-time is varied by pressing the foot pedal to adjust the amount of power that is delivered to the handpiece. In the illustrated example, the power increases linearly from an initial value to 40%, the on-time is fixed or constant, and the off-time decreases linearly from an initial value to 20 ms. For Burst mode, the initial value can be, for example 2500 ms. Indeed, other initial values can also be used.

Figure 14:
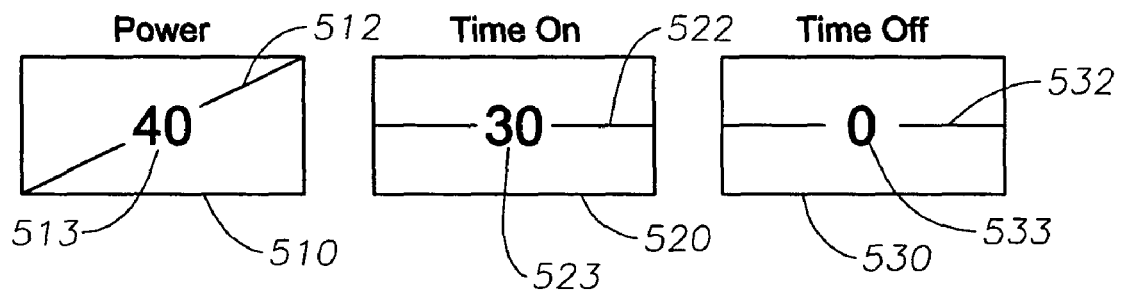
FIG. 14 illustrates an interface according to one embodiment that is set for "continuous" mode in which the off-time is set to zero.

FIG. 14 illustrates one exemplary implementation of "Continuous" mode. A continuous mode can be selected by setting the off-time to zero when in "Pulse" mode (FIG. 12) or other modes besides "Burst" mode (FIG. 13). Ultrasound power is applied continuously in "Continuous" mode and in a linear manner so that the power increases linearly from zero to 40 as the foot pedal is pressed.

Figure 15:
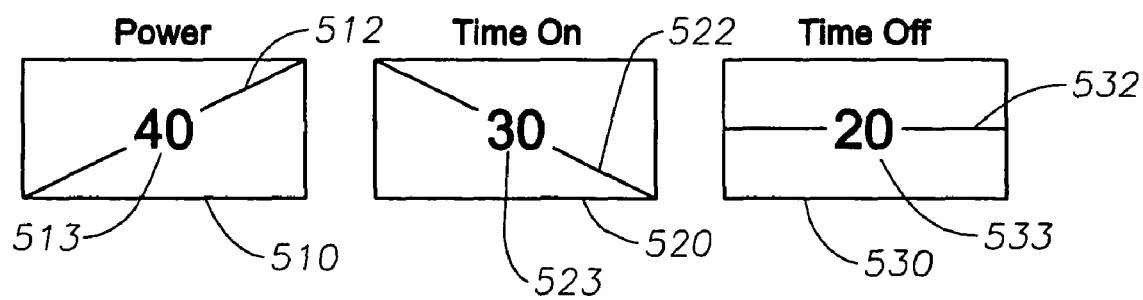
FIG. 15 illustrates an interface according to one embodiment that is set for a mode in which on-time decreases and the off-time remains constant relative to foot pedal displacement.

FIG. 15 illustrates a mode in which the on-time decreases linearly and the off-time remains constant as the foot pedal is pressed. More particularly, this combination results in power increasing linearly from an initial value to 40%, the on-time decreasing linearly from an initial value, such as 150 ms (a factor of five times the ending value) to the ending value of 30 ms in a linear manner. The off-time remains fixed at 20 ms. This particular mode can be beneficial since the pulses that are generated by the system can be "adaptive" to various lens hardnesses. For example, when the surgeon sees that a given foot pedal depression does not result in sufficiently rapid progress in lens removal, the surgeon will typically command deeper foot pedal penetration, thus resulting in greater power. Usually, greater power will result in increased repulsion, however, repulsion can be reduced, minimized or eliminated since the duration of the ultrasound pulse with this particular setting will be shortened. This result can be particularly useful when a surgeon is attempting to extract extremely mature cataracts, which are more prone to repulsion at higher powers due to their hardness.

Figure 16:
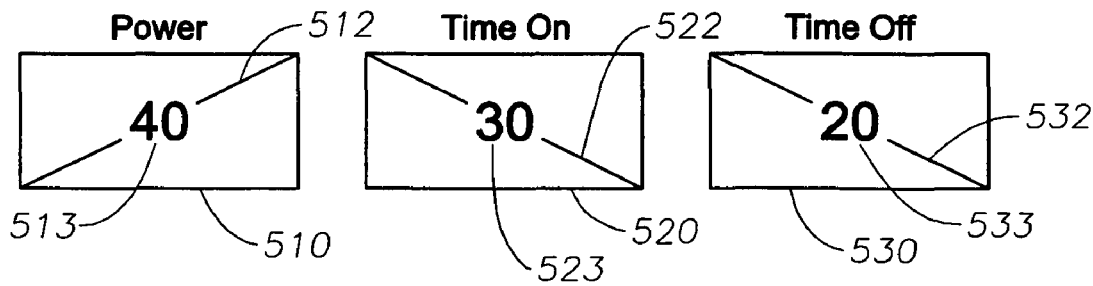
FIG. 16 illustrates an interface according to one embodiment that is set for a mode in which both the on-time and the off-time decrease relative to foot pedal displacement.

FIG. 16 illustrates a mode in which the power of pulses increases linearly from an initial value to 40%, the on-time decreases linearly from an initial value, such as 150 ms, to a minimum value of 30 ms, and the off-time decreases linearly from an initial value, such as 2500 ms, to a minimum value of 20 ms.

Figure 17:
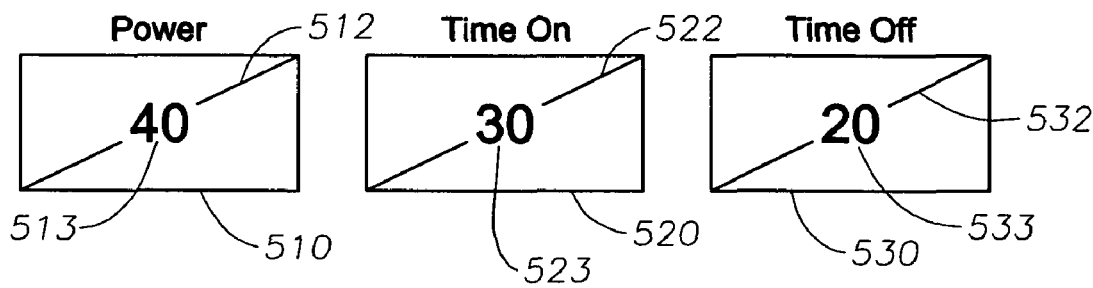
FIG. 17 illustrates an interface according to one embodiment that is set for a mode in which both the on-time and the off-time increase relative to foot pedal displacement.

FIG. 17 illustrates a mode in which the power, on-time and off-time all increase linearly as the foot pedal is pressed. The power increases linearly from an initial value zero to 40%, the on-time increases linearly from an initial value, e.g., 6 ms, to 20 ms, and the off-time increases linearly from an initial value, e.g. 4 ms, to 20 ms.

Figure 18:
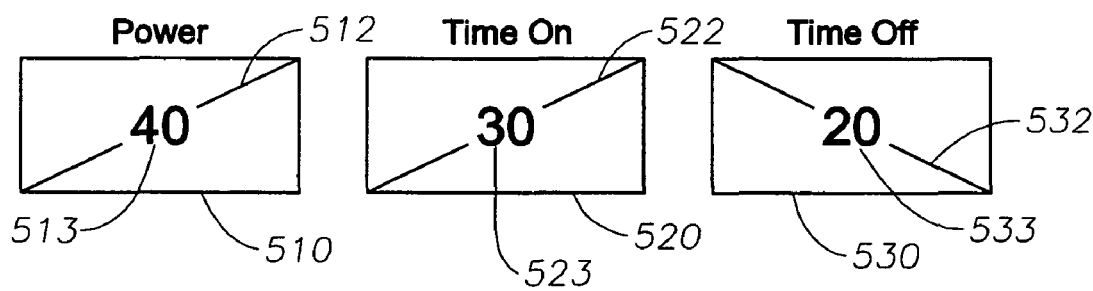
FIG. 18 illustrates an interface according to one embodiment that is set for a mode in which the on-time increases and the off-time decreases relative to foot pedal displacement.

FIG. 18 illustrates a mode in which the power and on-time increase linearly and the off-time decreases linearly. The power increases linearly from an initial value to 40%, the on-time increases linearly from 6 ms, to 30 ms, and the off-time decreases linearly from an initial value, e.g., 2500 ms, to 20 ms.

Figure 19:
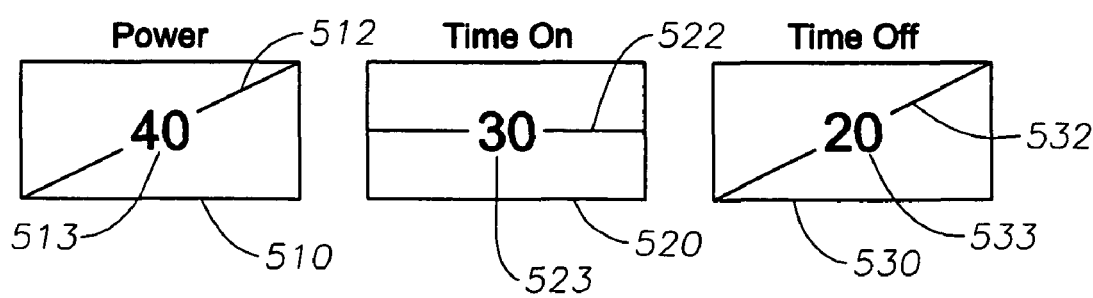
FIG. 19 illustrates an interface according to one embodiment that is set for a mode in which the on-time remains constant and the off-time decreases relative to foot pedal displacement.

FIG. 19 illustrates a mode in which the power increases linearly from the initial value to 40%, the on-time remains constant at 30 ms, and the off-time increases linearly from 4 ms to 20 ms as the foot pedal is pressed.

Figure 20:
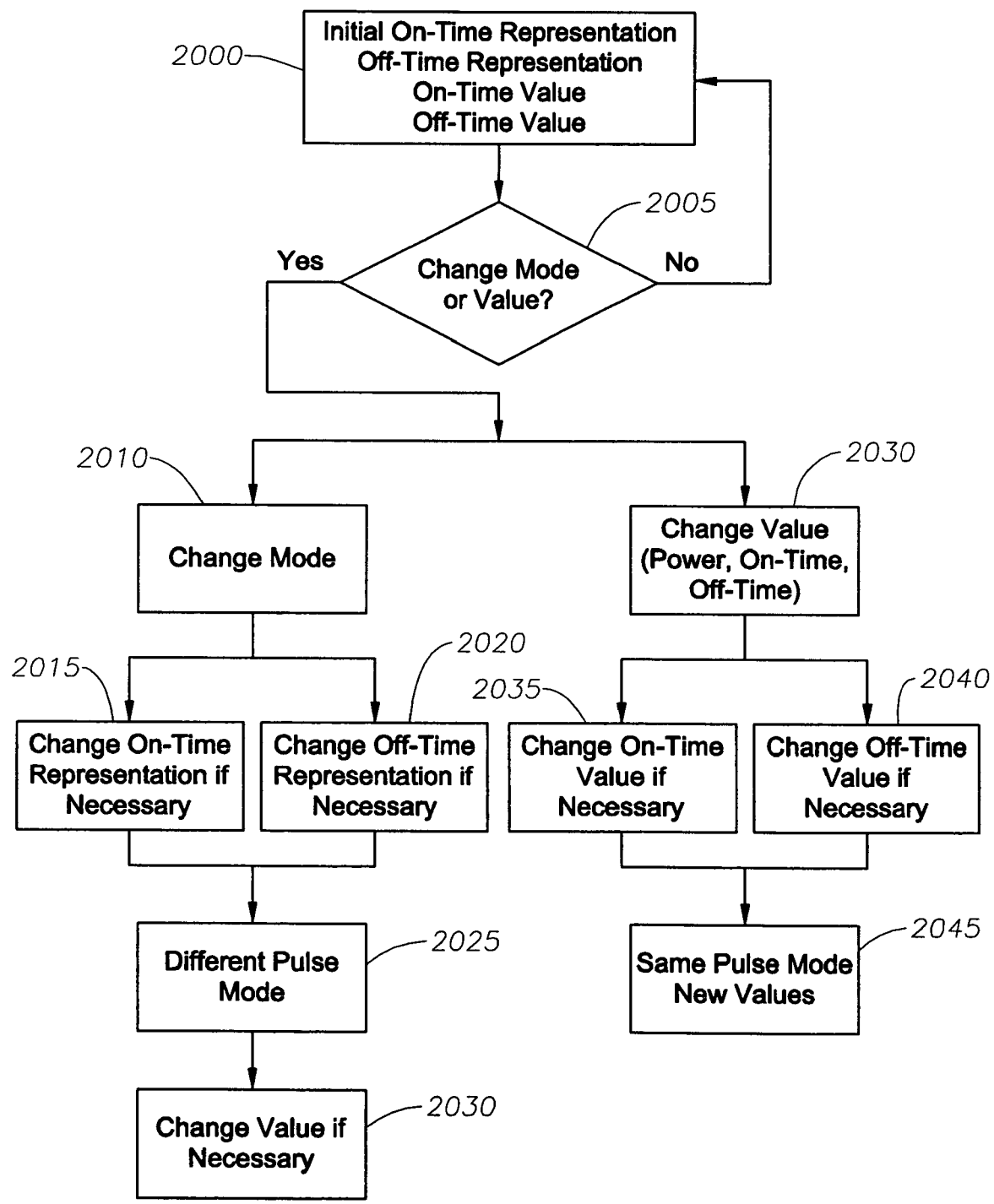
FIG. 20 is a flow chart illustrating a method for selecting a mode and related on-time and off-time values according to one embodiment.

FIG. 20 illustrates a method in which representations and on-time and off-time values can be adjusted. In step 2000, the phacoemulsification surgery system is configured to have an initial on-time representation, an initial off-time representation, an initial on-time value, and an initial off-time value. In step 2005, a decision is made whether the pulse mode or a value of a pulse parameter are to be changed. If not, the initial settings are maintained.

If the pulse mode is to be changed, in step 2010, then the on-time and off-time representations are changed as necessary in steps 2015 and 2020. For example, the surgeon can touch the display screen at an on-time display element to change the on-time representation to one of an increasing linear, constant or decreasing linear representation. Similarly, the surgeon can touch the display screen at an off-time display element to change the off-time representation to one of an increasing linear, constant or decreasing linear representation. The selected combination of the on-time and off-time functions results in one of pulse modes shown in FIG. 11 being selected in step 2025. Of course, different numbers of representations can allow a surgeon to generate different number of pulse modes.

The values of the on-time and off-time parameters can be adjusted in step 2030. More specifically, the on-time value and the off-time value can be adjusted as necessary in steps 2035 and 2040. Thus, the values of the pulse mode are adjusted in step 2045 as necessary.

Persons skilled in the art will recognize that the graphical user interface and adjustments to the on-time and the off-time can be modified in various ways. Accordingly, persons of ordinary skill in the art will appreciate that embodiments are not limited to the particular exemplary embodiments described, but rather, embodiments can be applied to other surgical equipment and parameters. Although references have been made in the foregoing description to various embodiments, persons of ordinary skill in the art will recognize that insubstantial modifications, alterations, and substitutions can be made to the described embodiments without departing from the invention as claimed in the accompanying claims.

What is claimed:

1. A user interface for a phacoemulsification surgical system that generates pulses having an on-time and an off-time, the pulses being adjusted in response to a foot pedal and based on settings in the user interface displayed on a display screen, the user interface comprising:

a first display element comprising a representation of the on-time of the pulses generated by the phacoemulsification surgical system relative to a position of the foot pedal, wherein the representation of the on-time of the pulses is a decreasing linear representation, a decreasing non-linear representation, a horizontal representation, an increasing linear representation, or an increasing non-linear representation, and wherein each representation of the on-time of the pulses is sequentially displayed in a menu in response to touching of the display screen at the first display element;

an on-time value that is displayed with the first display element and that indicates a value of the on-time of the pulses, wherein the representation of the on-time of the pulses is displayed in a background relative to the on-time value;

a second display element comprising a representation of the off-time of the pulses generated by the phacoemulsification surgical system relative to a position of the foot pedal, wherein the representation of the off-time of the pulses is a decreasing linear representation, a decreasing non-linear representation, a horizontal representation, an increasing linear representation, or an increasing non-linear representation, and wherein each representation of the off-time of the pulses is sequentially displayed in a menu in response to touching the display screen at the second display element; and an off-time value display that is displayed with the second display element and that indicates a value of the off-time of the pulses, wherein the representation of the off-time value display appears within the second display element and the representation of the off-time of the pulses is displayed in a background relative to the off-time value.

* * * * *